(12) United States Patent
Chen et al.

(10) Patent No.: US 6,737,532 B2
(45) Date of Patent: May 18, 2004

(54) ORGANIC ELECTROLUMINESCENT MATERIALS

(75) Inventors: Ruey-Min Chen, Keelung (TW); Jun-Wen Chung, Kaohsiung Hsien (TW)

(73) Assignees: Chi Mei Optoelectronics Corporation, Tainan (TW); Kyocera Corporation, Kyoto (JP)

( * ) Notice: Subject to any disclaimer, the term of this patent is extended or adjusted under 35 U.S.C. 154(b) by 33 days.

(21) Appl. No.: 10/117,408

(22) Filed: Apr. 5, 2002

(65) Prior Publication Data

US 2002/0195930 A1 Dec. 26, 2002

(30) Foreign Application Priority Data

May 8, 2001 (TW) .......................... 90110908 A

(51) Int. Cl.⁷ ...................... C07D 277/62; C07D 263/62
(52) U.S. Cl. ...................... 548/156; 548/219
(58) Field of Search ................... 548/156, 219

(56) References Cited

U.S. PATENT DOCUMENTS

| | | |
|---|---|---|
| 4,769,292 A | 9/1988 | Tang et al. |
| 5,126,214 A | 6/1992 | Tokailin et al. |
| 5,130,603 A | 7/1992 | Tokailin et al. |
| 6,020,078 A | 2/2000 | Chen et al. |

FOREIGN PATENT DOCUMENTS

JP  11283747  * 10/1999

* cited by examiner

Primary Examiner—Deborah C. Lambkin
(74) Attorney, Agent, or Firm—Merchant & Gould P.C.

(57) ABSTRACT

An organic electroluminescent compound of the formula (I)

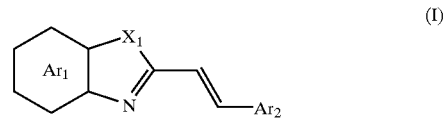

(I)

wherein:

$X_1$ is selected from the group consisting of oxygen, sulfur, $C(CH_3)_2$ and N—R, wherein R is hydrogen, alkyl of from 1 to 20 carbon atoms or aryl; and $Ar_1$ and $Ar_2$ are individually aryl or heterocyclic systems.

Applying the compound to an electroluminescent (EL) device provides a highly efficient blue and green emitting organic EL device.

8 Claims, 2 Drawing Sheets

ORGANIC ELECTROLUMINESCENT MATERIALS

BACKGROUND OF THE INVENTION

1. Field of the Invention

The present invention relates in general to an organic electroluminescent(EL) material. In particular, the present invention relates to a high efficiency blue and green organic EL material.

2. Description of the Related Art

An Organic Light Emitting Diode (OLED) with high efficiency was reported by C. W. Tang and S. A. Vanslyke in 1987. Device improvements incorporating fluorescent dyes in the emitter layers were demonstrated in 1989. Since then, flat panel display development based on OLEDs, has accelerated rapidly. In recent years, several laboratories around the world have been engaged in developing the materials, devices and processes needed to bringing this technology to commercialization.

FIG. 1 shows a schematic diagram of the conventional single layer OLED device structure. The substrate 8 is an electrically insulating and optically transparent material such as glass or plastic. Anode 6 is located on the substrate 8 and separated from cathode 2 by an organic EL medium 4. The anode 6 and the cathode 2 are connected to an external AC or DC power source 5. In operation, the device can be viewed as a diode that is forward biased when the anode 6 is at a higher potential then the cathode 2. Under these conditions, holes (positive charge carriers) and electrons are injected from the anode 6 and the cathode 2 into the organic EL medium 4, respectively. This results in hole-electron recombination and a release of energy in part as light, thus producing electroluminescence.

FIG. 2 is a schematic diagram of the conventional double layer OLED device structure. The substrate 20 is an electrically insulating and optically transparent material such as glass or plastic. Anode 18 is located on the substrate 20 and separated from cathode 12 by an electron-transport layer 14 and a hole-transport layer 16. The hole-transport layer 16 is formed on the anode 18. Located above the hole-transport layer 16 is the electron-transport layer 14. The anode 6 and the cathode 2 are connected to an external AC or DC power source 15. In the double layer OLED device structure, the hole-transport layer 16 is specifically chosen to inject and transport holes, and the electron-transport layer 14 is specifically chosen to inject and transport electrons. The interface between the two layers provides an efficient site for the recombination of the injected hole-electron pair and resultant electroluminescence. Moreover, the double layer structure has been developed to multilayer structure, and the multilayer structure including electron-inject layer, electron-transport layer, hole-inject layer, hole-transport layer, and emissive layer, etc.

Typical organic emitting materials were formed of a conjugated organic host material and a conjugated organic activating agent having condensed benzene rings. However, for the production of full color OLED display panel, it is necessary to have efficient red, green and blue (RGB) EL materials with proper chromaticity and sufficient luminance efficiency. The guest-host doped system offers a ready avenue for achieving such an objective, mainly because doping an emissive dopant (guest) of high luminescent property into a host can raise the efficiency of radiative recombination. Therefore, it is very important to open up new and efficient organic EL materials.

SUMMARY OF THE INVENTION

An object of the present invention is to provide an organic electroluminescent compound of the formula (I):

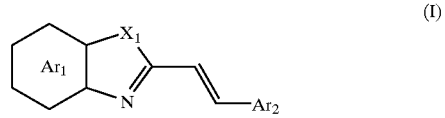

(I)

wherein:

$X_1$ is selected from oxygen, sulfur, $C(CH_3)_2$ and N—R, wherein R is hydrogen, alkyl of from 1 to 20 carbon atoms or aryl; and $Ar_1$ and $Ar_2$ are individually aryl or heterocyclic systems.

$Ar_1$ is shown as:

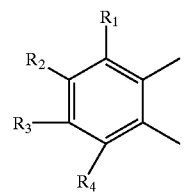

wherein:

$R_1$, $R_2$, $R_3$ and $R_4$ are individually selected from the group consisting of hydrogen, halogen, substituted or unsubstituted alkyl group, substituted or unsubstituted alkoxy group, substituted or unsubstituted thioalkyl group, substituted or unsubstituted arylene group, substituted or unsubstituted aryloxy group, substituted or unsubstituted arylthio group, substituted or unsubstituted arylamino group, substituted or unsubstituted carbocyclic aromatic group, substituted or unsubstituted heterocyclic aromatic group, nitro group, and cyano group.

$Ar_2$ is selected from the group consisting of substituted or unsubstituted biphenylene, substituted or unsubstituted triphenylene, substituted or unsubstituted terephenylene, substituted or unsubstituted bithiophene, substituted or unsubstituted trithiophene, substituted or unsubstituted terephenylene, substituted or unsubstituted arylene vinylene, substituted or unsubstituted carbazole, substituted or unsubstituted arylamino group, substituted or unsubstituted carbocyclic aromatic group, and substituted or unsubstituted heterocyclic aromatic group.

Another object of the present invention is to provide an organic electroluminescent compound of the formula (II):

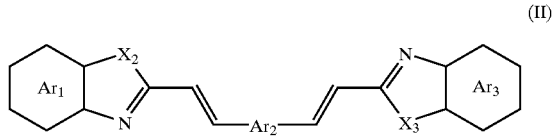

(II)

wherein:

$X_2$ and $X_3$ are individually selected from the group consisting of oxygen, sulfur, $C(CH_3)_2$ and N—R, wherein R is hydrogen, alkyl of from 1 to 20 carbon atoms or aryl; and $Ar_1$, $Ar_2$ and $Ar_3$ are individually aryl or heterocyclic systems.

$Ar_1$ and $Ar_3$ are shown as:

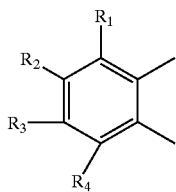

wherein:

$R_1$, $R_2$, $R_3$ and $R_4$ are individually selected from the group consisting of hydrogen, halogen, substituted or unsubstituted alkyl group, substituted or unsubstituted alkoxy group, substituted or unsubstituted thioalkyl group, substituted or unsubstituted arylene group, substituted or unsubstituted aryloxy group, substituted or unsubstituted arylthio group, substituted or unsubstituted arylamino group, substituted or unsubstituted carbocyclic aromatic group, substituted or unsubstituted heterocyclic aromatic group, nitro group, and cyano group.

$Ar_2$ is selected from the group consisting of substituted or unsubstituted biphenylene, substituted or unsubstituted triphenylene, substituted or unsubstituted terephenylene, substituted or unsubstituted bithiophene, substituted or unsubstituted trithiophene, substituted or unsubstituted terephenylene, substituted or unsubstituted arylene vinylene, substituted or unsubstituted carbazole, substituted or unsubstituted arylamino group, substituted or unsubstituted carbocyclic aromatic group, and substituted or unsubstituted heterocyclic aromatic group.

Applying the above-mentioned compounds of the present invention to an EL device provides a highly efficient blue and green emitting organic EL device.

BRIEF DESCRIPTION OF THE DRAWINGS

The present invention can be more fully understood by reading the subsequent detailed description in conjunction with the examples and references made to the accompanying drawings, wherein.

DETAILED DESCRIPTION OF THE PREFERRED EMBODIMENT

Figure 1:
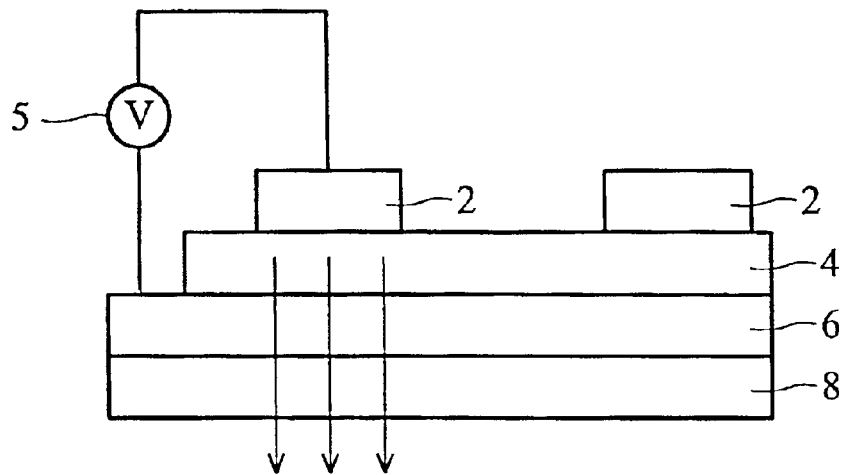
FIG. 1 is a schematic diagram of the conventional single layer OLED device structure.
Figure 2:
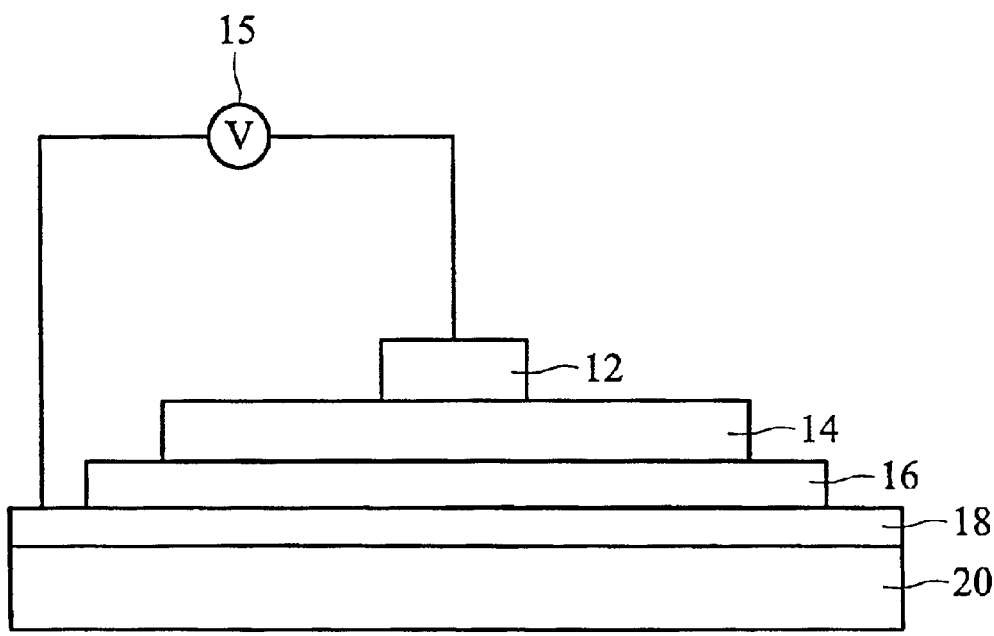
FIG. 2 is a schematic diagram of the conventional double layer OLED device structure.

The present invention generally relates to an organic electroluminescent compound of the formula (I):

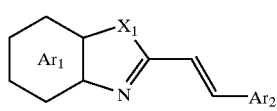

(I)

Wherein: $X_1$ is selected from the group consisting of oxygen, sulfur, $C(CH_3)_2$ and N—R, wherein R is hydrogen, alkyl of from 1 to 20 carbon atoms or aryl; $Ar_1$ and $Ar_2$ are individually aryl or heterocyclic systems.

In the above-mentioned $Ar_1$, for example, is preferably showed as following formula:

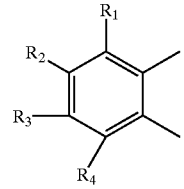

Wherein: $R_1$, $R_2$, $R_3$ and $R_4$ are individually selected from the group consisting of hydrogen, halogen, substituted or unsubstituted alkyl group, substituted or unsubstituted alkoxy group, substituted or unsubstituted thioalkyl group, substituted or unsubstituted arylene group, substituted or unsubstituted aryloxy group, substituted or unsubstituted arylthio group, substituted or unsubstituted arylamino group, substituted or unsubstituted carbocyclic aromatic group, substituted or unsubstituted heterocyclic aromatic group, nitro group, and cyano group.

In the above-mentioned $Ar_2$, for example, is preferably selected from the group consisting of substituted or unsubstituted biphenylene, substituted or unsubstituted triphenylene, substituted or unsubstituted terephenylene, substituted or unsubstituted bithiophene, substituted or unsubstituted trithiophene, substituted or unsubstituted terephenylene, substituted or unsubstituted arylene vinylene, substituted or unsubstituted carbazole, substituted or unsubstituted arylamino group, substituted or unsubstituted carbocyclic aromatic group, and substituted or unsubstituted heterocyclic aromatic group.

In another aspect, the invention relates to an organic electroluminescent compound of the formula (II):

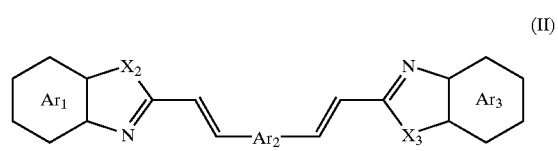

(II)

wherein: $X_2$ and $X_3$ are individually selected from the group consisting of oxygen, sulfur, $C(CH_3)_2$ and N—R, wherein R is hydrogen, alkyl of from 1 to 20 carbon atoms or aryl; $Ar_1$, $Ar_2$ and $Ar_3$ are individually aryl or heterocyclic systems.

In the above-mentioned $Ar_1$ and $Ar_3$, for example, are preferably showed as:

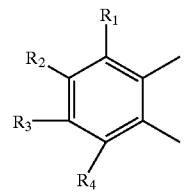

wherein: $R_1$, $R_2$, $R_3$ and $R_4$ are individually selected from the group consisting of hydrogen, halogen, substituted or unsubstituted alkyl group, substituted or unsubstituted alkoxy group, substituted or unsubstituted thioalkyl group, substituted or unsubstituted arylene group, substituted or unsubstituted aryloxy group, substituted or unsubstituted arylthio group, substituted or unsubstituted arylamino group, substituted or unsubstituted carbocyclic aromatic group, substituted or unsubstituted heterocyclic aromatic group, nitro group, and cyano group.

In the above-mentioned $Ar_2$, for example, is preferably selected from the group consisting of substituted or unsubstituted biphenylene, substituted or unsubstituted triphenylene, substituted or unsubstituted terephenylene, substituted or unsubstituted bithiophene, substituted or unsubstituted trithiophene, substituted or unsubstituted terephenylene, substituted or unsubstituted arylene vinylene, substituted or unsubstituted carbazole, substituted or unsubstituted arylamino group, substituted or unsubstituted carbocyclic aromatic group, and substituted or unsubstituted heterocyclic aromatic group.

Applying the above-mentioned compounds of the present invention to an EL device provides an improved blue and green emitting organic EL device.

Without intending to limit it in any manner, the present invention will be further illustrated by the following examples.

EXAMPLES

Example 1

One preferred blue organic electroluminescent compound of the present invention is described as follows.

2-methyl-benzothiazole (compound 1) of 1.49 g (10 mmol) and p-4-bromobenzaldehyde (compound 2) of 1.86 g (10 mmol) were dissolved in 10 ml of tetrahydrofuran (THF) to form a solution, and potassium hydroxide of 0.4 g was added into the solution. The above mixture solution was further reacted at room temperature for 5 hours to give a compound A of 1.6 g (yield=51%).

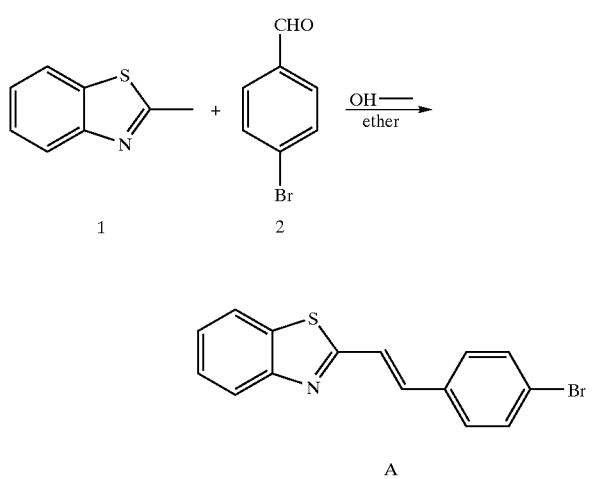

Afterwards, compound A (1.58 g, 5 mmol) and vinyl biphenyl compound 3 (0.9 g, 5 mmol) were heated and refluxed in dimethylformanide (DMF) of 25 ml for 24 hours under the catalysts of Pd(OAc)$_2$ (43 mg, 0.2 mmol) and P(o-tolyl)$_3$ (0.24 g, 0.8 mmol) to give a compound B of 1.6 g (yield=77%). The measurement of fluorescent emission $\lambda_{max}$ of the compound B was 458 nm.

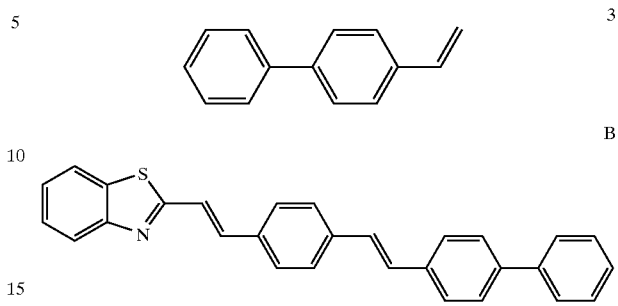

Example 2

Another preferred blue organic electroluminescent compound of the present invention is described as follows.

2-methyl-benzothiazole (compound 1) of 1.49 g (10 mmol) and p-vinylbenzaldehyde (compound 4) of 1.32 g (10 mmol) were dissolved in 10 ml of THF to form a solution, and potassium hydroxide of 0.4 g was added into the solution. The above mixture solution was further reacted at room temperature for 5 hours to give a compound C of 1.4 g (yield=50%).

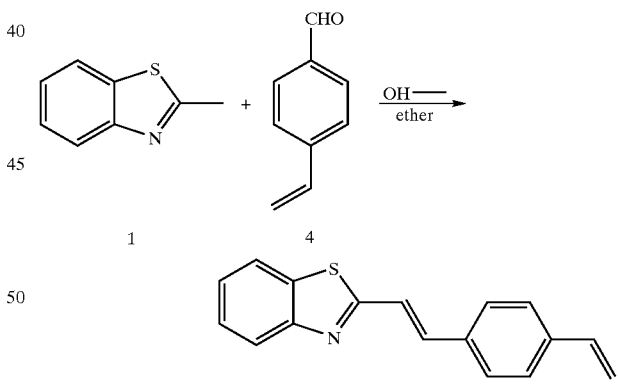

Afterwards, compound C (1.3 g, 5 mmol) and 4,4'-diiodo phenyl benzene (compound 5, 2.1 g, 5 mmol) were heated and refluxed in DMF of 25 ml for 24 hours under the catalysts of Pd(OAc)$_2$ (43 mg, 0.2 mmol) and P(o-tolyl)$_3$ (0.24 g, 0.8 mmol) to give a compound D of 2.7 g (yield= 80%). The measurement of fluorescent emission $\lambda_{max}$ of the compound D was 452 nm.

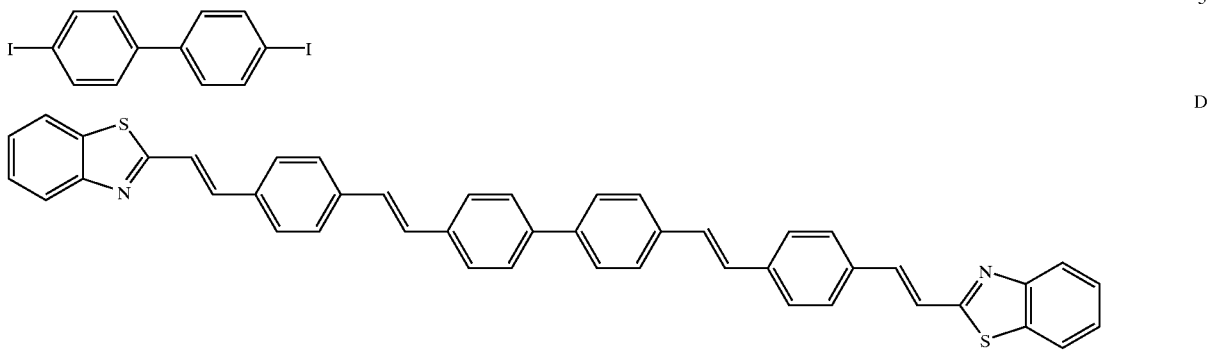

D

Example 3

One preferred green organic electroluminescent compound of the present invention is described as follows.

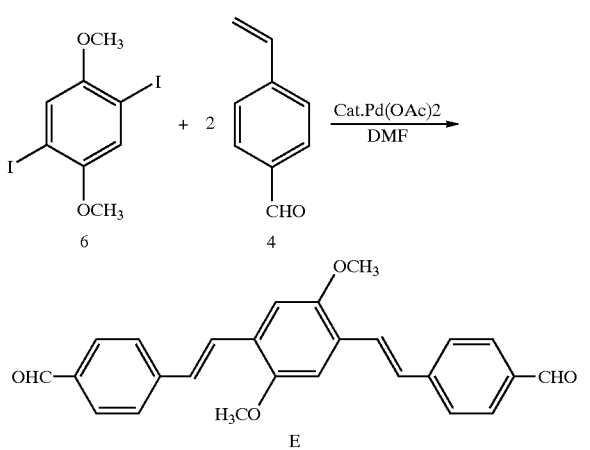

Compound 6 (1.94 g, 5 mmol) and p-vinylbenzaldehyde (compound 4, 1.32 g, 10 mmol) were heated and refluxed in DMF of 25 ml for 24 hours under the catalysts of $Pd(OAc)_2$ (43 mg, 0.2 mmol) and $P(o-tolyl)_3$ (0.24 g, 0.8 mmol) to give a compound E of 1.55 g (yield=80%).

Afterwards, the above compound 1 of 1.27 g (8 mmol) and the compound E of 1.52 g (4 mmol) were dissolved in 10 ml of methanol to form a solution, and potassium hydroxide of 0.32 g was added into the solution. The above mixture solution was further reacted at room temperature for 5 hours to give a compound F of 1.1 g (yield=40%). The measurement of fluorescent emission $\lambda_{max}$ of the compound F was 505 nm.

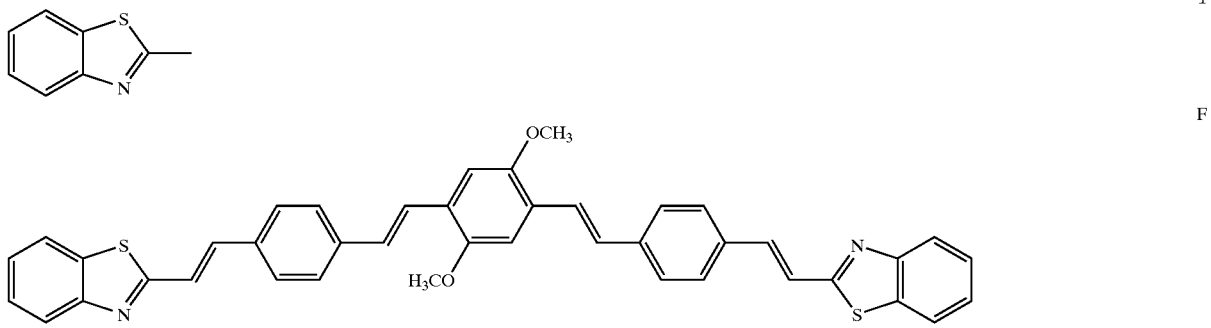

F

Example 4

Another preferred green organic electroluminescent compound of the present invention is described as follows.

2,3,3-trimethyl-4,5-benzo-3H-indole(compound 7, 2.09 g, 10 mmol) and compound 8 (2.73 g, 10 mmol) were dissolved in 10 ml of methanol to form a solution, and then potassium hydroxide of 0.4 g was added into the solution. The above mixture solution was further reacted at room temperature for 5 hours to give a compound G of 1.9 g (yield=40%). The measurement of fluorescent emission $\lambda_{max}$ of the compound F was 539 nm.

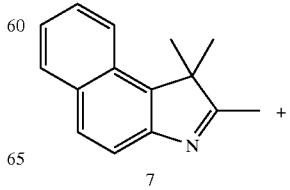

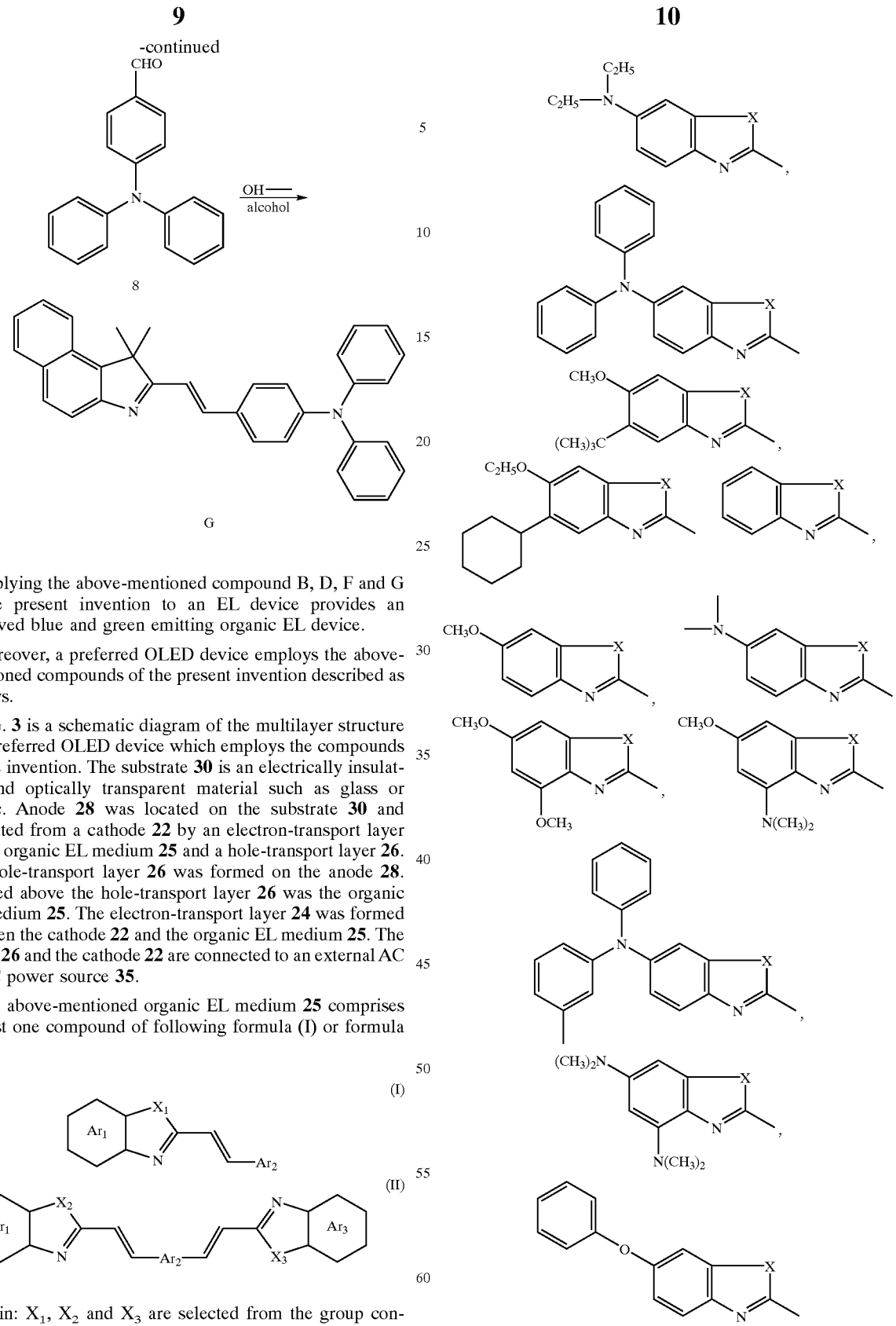

Applying the above-mentioned compound B, D, F and G of the present invention to an EL device provides an improved blue and green emitting organic EL device.

Moreover, a preferred OLED device employs the above-mentioned compounds of the present invention described as follows.

Figure 3:
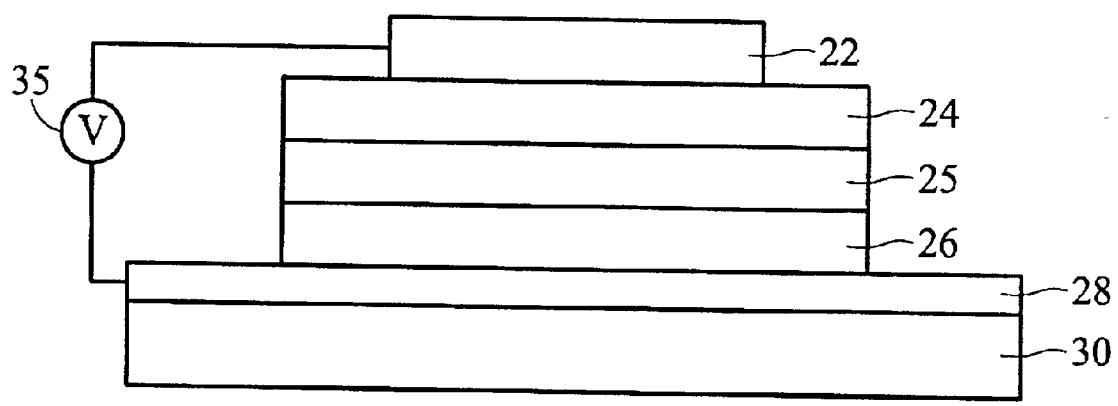
FIG. 3 is a schematic diagram of the multilayer structure of a preferred OLED device which employs the compound of this invention.

FIG. 3 is a schematic diagram of the multilayer structure of a preferred OLED device which employs the compounds of this invention. The substrate 30 is an electrically insulating and optically transparent material such as glass or plastic. Anode 28 was located on the substrate 30 and separated from a cathode 22 by an electron-transport layer 24, an organic EL medium 25 and a hole-transport layer 26. The hole-transport layer 26 was formed on the anode 28. Located above the hole-transport layer 26 was the organic EL medium 25. The electron-transport layer 24 was formed between the cathode 22 and the organic EL medium 25. The anode 26 and the cathode 22 are connected to an external AC or DC power source 35.

The above-mentioned organic EL medium 25 comprises at least one compound of following formula (I) or formula (II):

wherein: $X_1$, $X_2$ and $X_3$ are selected from the group consisting of oxygen, sulfur, $C(CH_3)_2$ and N—R, wherein R is hydrogen, alkyl of from 1 to 20 carbon atoms or aryl; $Ar_1$, $Ar_2$ and $Ar_3$ are individually aryl or heterocyclic systems.

Further, the above $Ar_1$ and $Ar_3$ are selected from the group consisting of:

wherein: the above X is selected from the group consisting of oxygen, sulfur, N—$CH_3$ and

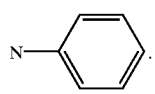

Moreover, the above Ar$_2$ is selected from the group consisting of:

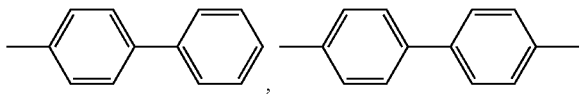

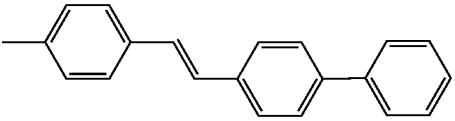

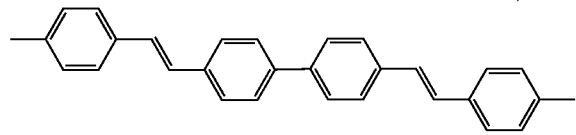

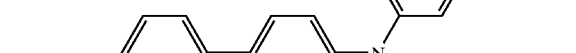
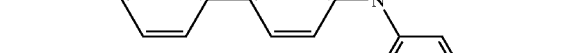
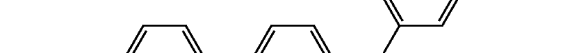
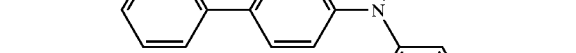
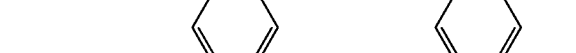
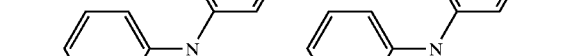
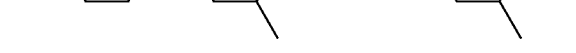

-continued

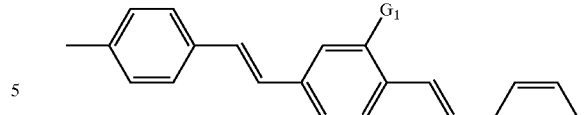

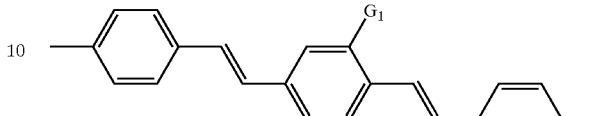

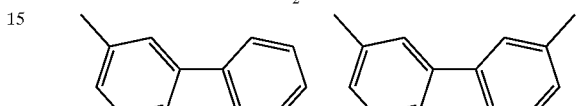

wherein: $G_1$ and $G_2$ are selected from the group consisting of methyl, ethyl, propyl, n-butyl, methoxyl, ethoxyl, propoxyl, phenyl, tolyl and biphenyl; $G_3$ is selected from the group consisting of methyl, ethyl, propyl, n-butyl, phenyl, tolyl and biphenyl.

While the invention has been particularly shown and described with reference to the preferred embodiment thereof, it will be understood by those skilled in the art that various changes in form and details may be made without departing from the spirit and scope of the invention.

What is claimed is:

1. An organic electroluminescent compound of the formula (I):

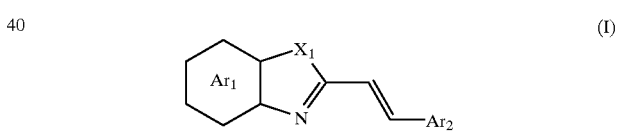

(I)

wherein:

$X_1$ is selected from the group consisting of oxygen, sulfur, $C(CH_3)_2$ and N—R, wherein R is hydrogen, alkyl of from 1 to 20 carbon atoms or aryl; and Ar$_1$ is an aryl or heterocyclic system, and Ar$_2$ is selected from the group consisting of substituted or unsubstituted biphenylene, substituted or unsubstituted triphenylene, substituted or unsubstituted terephenylene, substituted or unsubstituted bithiophene, substituted or unsubstituted trithiophene, substituted or unsubstituted terephenylene, substituted or unsubstituted arylene vinylene, substituted or unsubstituted carbazole, substituted or unsubstituted arylamino group, and substituted or unsubstituted carbocyclic aromatic group.

2. The organic electroluminescent compound as claimed in claim 1, wherein Ar$_1$ is shown as:

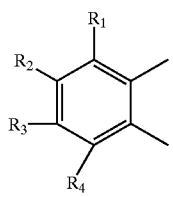

wherein:
$R_1$, $R_2$, $R_3$ and $R_4$ are individually selected from the group consisting of hydrogen, halogen, substituted or unsubstituted alkyl group, substituted or unsubstituted alkoxy group, substituted or unsubstituted thioalkyl group, substituted or unsubstituted arylene group, substituted or unsubstituted aryloxy group, substituted or unsubstituted arylthio group, substituted or unsubstituted arylamino group, substituted or unsubstituted carbocyclic aromatic group, substituted or unsubstituted heterocyclic aromatic group, nitro group, and cyano group.

3. An organic electroluminescent compound of the formula(II):

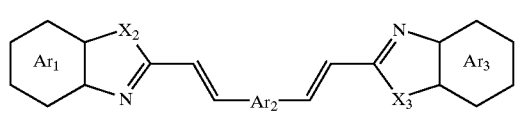

wherein:
$X_2$ and $X_3$ are individually selected from the group consisting of oxygen, sulfur, $C(CH_3)_2$ and N—R, wherein R is hydrogen, alkyl of from 1 to 20 carbon atoms or aryl; and $Ar_1$ and $Ar_3$ are individually aryl or heterocyclic systems, and $Ar_2$ is selected from the group consisting of substituted or unsubstituted triphenylene, substituted or unsubstituted terephenylene, substituted or unsubstituted bithiophene, substituted or unsubstituted trithiophene, substituted or unsubstituted terephenylene, substituted or unsubstituted arylene vinylene, substituted or unsubstituted carbazole, substituted or unsubstituted arylamino group, substituted or unsubstituted carbocyclic aromatic group, and substituted or unsubstituted heterocyclic aromatic group.

4. The organic electroluminescent compound as claimed in claim 3, wherein $Ar_1$ and $Ar_3$ are shown as:

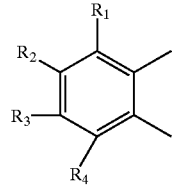

wherein:
$R_1$, $R_2$, $R_3$ and $R_4$ are individually selected from the group consisting of hydrogen, halogen, substituted or unsubstituted alkyl group, substituted or unsubstituted alkoxy group, substituted or unsubstituted thioalkyl group, substituted or unsubstituted arylene group, substituted or unsubstituted aryloxy group, substituted or unsubstituted arylthio group, substituted or unsubstituted arylamino group, substituted or unsubstituted carbocyclic aromatic group, substituted or unsubstituted heterocyclic aromatic group, nitro group, and cyano group.

5. The organic electroluminescent compound as claimed in claim 1, wherein changing a symmetry of $Ar_2$ changes a wavelength of emitted light.

6. The organic electroluminescent compound as claimed in claim 1, wherein changing a composition of $Ar_2$ changes a wavelength of emitted light.

7. The organic electroluminescent compound as claimed in claim 3, wherein changing a symmetry of $Ar_2$ changes a wavelength of emitted light.

8. The organic electroluminescent compound as claimed in claim 3, wherein changing a composition of $Ar_2$ changes a wavelength of emitted light.

* * * * *